United States Patent [19]

Abblard et al.

[11] 4,313,957
[45] Feb. 2, 1982

[54] PESTICIDAL SULFUR CONTAINING AMIDES DERIVED FROM ANILINE AND THE METHOD OF PREPARATION THEREOF

[75] Inventors: Jean Abblard, St. Didier au Mont d'Or; Guy Lacroix, Lyons, both of France

[73] Assignee: Rhone-Poulenc Agrochimie, France

[21] Appl. No.: 114,519

[22] Filed: Jan. 23, 1980

[30] Foreign Application Priority Data

Jan. 24, 1979 [FR] France ................................. 79 02580

[51] Int. Cl.³ ..................... A01N 37/14; A01N 37/10; C07C 153/023
[52] U.S. Cl. .................................. 424/301; 424/309; 424/319; 260/455 R; 562/426; 560/9
[58] Field of Search .................... 260/455 R; 562/426; 560/9; 424/301, 309, 319

[56] References Cited

U.S. PATENT DOCUMENTS 4,151,299  4/1979  Hubele ................................. 562/426

Primary Examiner—John M. Ford
Assistant Examiner—Robert C. Whittenbaugh
Attorney, Agent, or Firm—Robert E. Burns; Emmanuel J. Lobato; Bruce L. Adams

[57] ABSTRACT

The invention relates to sulphur-containing products with an amide group, which are derived from aniline.

These compounds have the formula:

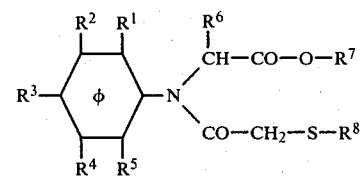

They are used as anti-fungal agents.

9 Claims, No Drawings

PESTICIDAL SULFUR CONTAINING AMIDES DERIVED FROM ANILINE AND THE METHOD OF PREPARATION THEREOF

The present invention relates to new sulphur-containing products with an amide group, which are derived from aniline. The invention also relates to the preparation of the said products and their application for the protection of plants, in particular against fungi and fungal diseases.

The products according to the invention have the formula

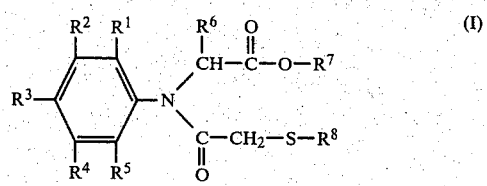

in which $R^1$ and $R^5$, which are identical or different, represent an alkyl or alkoxy radical having from 1 to 4 carbon atoms or a halogen atom or the hydrogen atom, it being possible for only one of the two radicals $R^1$ and $R^5$ to have this last meaning, $R^2$, $R^3$ and $R^4$, which are identical or different, represent the hydrogen atom or a halogen atom or an alkyl or alkoxy radical having from 1 to 4 carbon atoms, $R^6$ represents the hydrogen atom or a methyl radical, $R^7$ represents the hydrogen atom or an alkyl radical having from 1 to 12 carbon atoms or $(1/n)M^{n+}$, M being a cation of valency n and more particularly an ammonium cation (which is optionally substituted) or a metal cation, and $R^8$ represents the hydrogen atom or a radical of the formula $R^9$—CO—, in which $R^9$ is an organic radical which represents a linear or branched alkyl or alkenyl radical which has at most 18 carbon atoms and can be substituted by halogen atoms or hydroxyl, mercaptan, cyano or oxo groups or alkoxy, alkylthio, aryl, alkoxycarbonyl or acylamino radicals, these various radicals having at most 6 carbon atoms, a cycloalkyl radical which contains 3 to 7 carbon atoms in the ring (preferably cyclopropyl, cyclopentyl or cyclohexyl radicals) and can be substituted by halogen atoms or alkyl groups having at most 4 carbon atoms, a phenyl or naphthyl radical which is optionally substituted by halogen atoms or alkyl, acyloxy, acyl or alkoxy groups, these various groups having at most 6 carbon atoms, a heterocyclic radical containing, in the ring, 5 or 6 atoms of which 1 to 3 are oxygen, nitrogen or sulphur hetero-atoms, it being possible for this heterocyclic radical to be substituted by chlorine atoms or methyl or ethyl groups, and the free valency of this radical $R^9$ (i.e. the valency attached to the carbonyl group in the radical $R^9$—CO—) being carried by a carbon atom, or a radical comprising a heterocyclic group having the same meaning as that indicated in the preceding section, this heterocyclic group being joined to the carbonyl group (of $R^9$—CO—) via a divalent methylene or ethylene radical.

The substitution of a radical by an oxo group (that is to say by=O) corresponds, according to the usual terminology, to the presence of a carbonyl, group, —CO—, in this radical.

Amongst the halogen atoms which can be present in the substances represented by the formula (I), chlorine and bromine can be used in particular.

According to the definition given above, the group

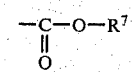

therefore represents a carboxyl or carboxylate group, it being possible for the bond in O—$R^7$ to be either of the covalent type (in particular in the case where —COO—$R^7$ represents an ester group) or of the ionic type (in particular in the case where —COO—$R^7$ represents a salt group) or of both types (in particular in the case of —COOH, which can be ionized or non-ionized or partially ionized).

If the group —COO—$R^7$ represents a salt group, it has been indicated that $R^7$ can then have the meaning $(1/n)M^{n+}$, M being a cation of valency n; in this case, the group —COO—$R^7$ can also be represented in the (formally more exact) form —COO$^\ominus$.$(1/n)M^{n+}$; however, this is also an average formula; the even more correct (but actually equivalent) representation of the molecule of the formula (I) is thus

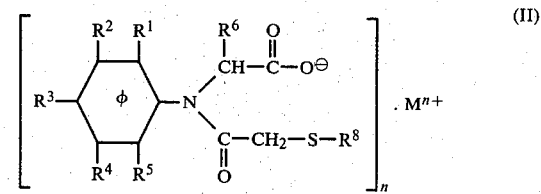

in which $R^1$, $R^2$, $R^3$, $R^4$, $R^5$, $R^6$, $R^8$, M and n have the meanings given above.

In the general family of compounds of the formula (I), such as it has now been defined, a particular subfamily is especially advantageous; in particular, it exhibits very good anti-fungal properties, especially with respect to Phycomycetes and more particularly with respect to mildews.

These preferred products are such that: $R^2$ represents a hydrogen, chlorine or bromine atom, $R^3$ and $R^4$ represent the hydrogen atom, $R^1$ and $R^5$ represent an alkyl group having from 1 to 4 carbon atoms, $R^6$ is the hydrogen atom or the methyl group and $R^7$ is an alkyl group having 1 to 4 carbon atoms and more especially the methyl radical.

In these families defined in this way, further preferred compounds have the formula in which $R^8$ represents the hydrogen atom or a radical $R^9$—CO— and $R^9$ represents an alkyl or alkenyl radical which is optionally substituted by chlorine atoms or alkoxy groups having from 1 to 4 carbon atoms or cyano, oxo, acetamido, phenyl, chlorophenyl, alkylthio or alkoxycarbonyl groups, a cyclopropyl, cyclopentyl or cyclohexyl radical, a phenyl radical which is optionally substituted by a chlorine or bromine atom, or a furyl, thienyl, trichlorothienyl or pyridyl heterocyclic radical.

The products in which $R^1$, $R^5$ and $R^7$ are the methyl radical and $R^9$ is an alkyl radical having from 1 to 9 carbon atoms are very especially advantageous.

The compounds according to the invention (of the formula I) can be prepared in accordance with several processes.

Some of the processes which can be used are respectively designated below by the letters (A), (B), (C) and (D) and correspond to the following equations:

PROCESS (A)

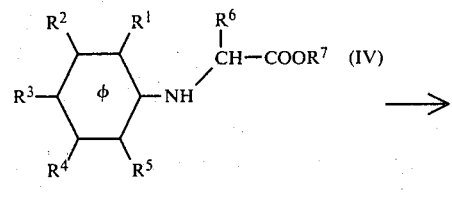

+

Cl—CO—CH$_2$—S—CO—R$^9$  (V)

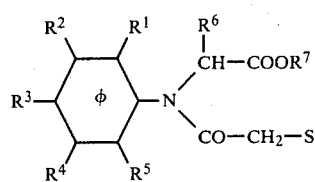

+ HCl

PROCESS (B)

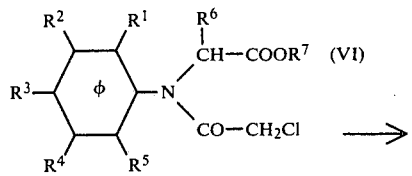

+

M'S—CO—R$^9$  (VII bis)

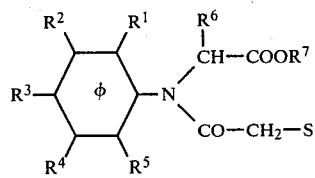

+ M'Cl

PROCESS (C)

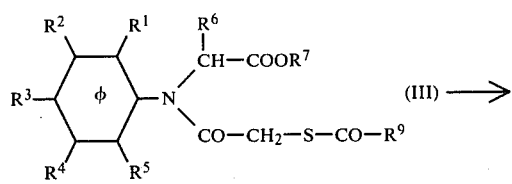

+ alcohol (e.g. R$^7$OH)

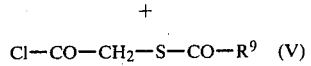

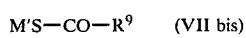

-continued (VIII)

+ ester (e.g. R$^9$COOR$^7$)

PROCESS (D)

(VIII)

+

R$^9$—CO—Cl
or (R$^9$CO)$_2$O (III)

In accordance with the first process, namely process (A), a compound of the formula (III) is obtained by reacting a N-phenyl-aminoacid derivative of the formula (IV) with an acid chloride of the formula (V), the symbols R$^1$ to R$^6$ and R$^8$ and R$^9$ having the meanings given above and the symbol R$^7$ representing the hydrogen atom or an alkyl radical.

The reaction employed in this process (A) is advantageously carried out in solution in an inert solvent (i.e. a solvent which does not react chemically with the reactants under the operating conditions). The reaction temperature is generally above 40° C. and below the degradation temperature of the reactants and/or reaction products. Thus, the temperature is generally between 60° and 150° C. In accordance with a convenient procedure, the reaction is carried out at the b.p. of the solvent in question. Polar or non-polar aprotic organic solvents may be mentioned as suitable solvents. It is preferred to use solvents which have a b.p. in the range indicated for the reaction temperature; solvents which can be used are therefore aromatic hydrocarbons (such as benzene, toluene, xylenes or chlorobenzene) or aliphatic hydrocarbons (such as hexane, heptane, cyclohexane or methylcyclohexane), chlorinated aliphatic hydrocarbons (such as dichloroethane, dichloroethylene, chloroform or carbon tetrachloride), ethers (such as dioxane, tetrahydrofurane or diethyl ether), ketones (such as acetone, methyl ethyl ketone or methyl isobutyl ketone) or nitriles (such as acetonitrile).

The reaction can be catalyzed, e.g. by dimethylformamide; it can be carried out in the absence or presence of a condensation agent, in particular an acid acceptor. Acid acceptors which can be used are tertiary amines, such as trialkylamines (e.g. triethylamine) or N-aryldialkylamines (e.g. N,N-dimethylaniline) or also pyridine and pyridine bases, or inorganic bases, such as alkali metal or alkaline earth metal carbonates and bicarbonates and sodium acetate. Furthermore, an excess of the amino compound of the formula (IV) can be used as the acid acceptor and this constitutes a preferred operating procedure.

The reaction can be carried out in the presence of an excess of one or other of the reactants. However, as has just been stated, a preferred procedure consists in carrying out the reaction in the presence of an excess of the compound of the formula (IV), at least during the first part of the reaction. The reaction can be carried out in the presence of an excess of the compound of the formula (IV), e.g. by gradually introducing the acid chloride of the formula (V) into the reaction medium containing all or part of the compound of the formula (IV) which is to be employed, and the reaction is then allowed to proceed until the evolution of hydrogen chloride ceases; the overall amounts of reactants employed during the reaction are preferably close to the stoichiometric amounts; it is generally most advantageous to use stoichiometric amounts; however, the acid chloride of the formula (V) can be employed in an amount which exceeds the stoichiometric amount, e.g. by up to 10% (in number). At the end of the reaction, the reaction product of the formula (III) is isolated by any means which is in itself known, e.g. by distillation of the solvent (i.e. evaporation) and/or crystallization of the product in the medium.

As regards the preparation of the compounds of the formula (IV), it can be carried out in accordance with similar processes to those described for the preparation of anilinoalkanecarboxylic acid esters in the following publications: J. Org. Chem., 30, pages 4,101–4,104 (1965), and Tetrahedron, 1967, pages 487–498.

The acid chlorides of the formula (V) can be prepared in accordance with or in a similar manner to many known processes, but especially the processes described in U.S. Pat. No. 2,412,700, Berichte, 46, pages 2,103–2,107 (1913), and Annalen, 602, pages 1–14 (1957).

In accordance with the second process, namely process (B), compounds of the formula (III), in which $R^1$ to $R^7$ and $R^9$ have the meanings given for the formula (I), are prepared; this preparation is carried out by reacting a N-phenyl-aminoacid derivative of the formula (VI) with an alkali metal thiocarboxylate or alkaline earth metal thiocarboxylate (preferably an alkali metal thiocarboxylate) derived from a thiocarboxylic acid of the formula $R^9$—CO—S—H (VII). The ammonium cation is included in the alkali metal cations which can be used. These thiocarboxylates can be represented by the formula $R^9$—CO—S—M' [formula (VII bis)], M' representing the alkali metal (or ammonium) cation or half an equivalent of an alkaline earth metal cation.

The derivatives of the formula (VI) can be prepared in accordance with processes which are identical or similar to those described in British Pat. No. 1,445,387.

A convenient method for the preparation of the alkali metal thiocarboxylate or alkaline earth metal thiocarboxylate obviously consists in reacting a thiocarboxylic acid with an alkali metal derivative or alkaline earth metal derivative, such as an alkali metal hydroxide or carbonate or alkaline earth metal hydroxide or carbonate. If the reaction is carried out in a solvent, a solution (or, if appropriate, a suspension) of the thiocarboxylate of the formula (VII bis) can thus be obtained direct.

The preparation of the compound of the formula (III) from the compounds of the formula (VI) and the thiocarboxylate is generally carried out in the presence of an inert solvent (i.e. a solvent which is chemically inert with respect to the reactants or reaction products under the operating conditions). The reaction temperature and the solvents which can be used are similar to those defined with reference to process (A). Additional solvents which can be used are amides (such as dimethylformamide) and sulphoxides (such as dimethylsulphoxide).

At the end of the reaction, the alkali metal chloride or alkaline earth metal chloride which has precipitated is separated off (e.g. by filtration) and the solvent is evaporated off; if necessary, customary purification operations can be carried out, such as e.g. washing an organic solution of the compound of the formula (III) with water.

In accordance with the third process, namely process (C), compounds of the formula (VIII), with a free mercaptan group, are prepared by reacting a compound of the formula (III) with an alcohol. If $R^7$ is an alkyl group, an alcohol of the formula $R^7$—OH is advantageously used; methanol is preferred amongst the alcohols which can be used. During the reaction carried out in this process (C), an ester (e.g. of the formula $R^9COOR^7$) is formed, whereupon the reaction is a transesterification in the broad sense. The reaction is preferably carried out in alcoholic (if appropriate methanolic) solution in the presence of an alkaline agent (or catalyst) (1st variant) or an acid agent (or catalyst) (2nd variant). The reaction temperature is generally between 0° and 120° C.

An alkali metal alcoholate, such as sodium methylate or potassium methylate (also referred to as methanolate), is preferably used as the alkaline agent (or catalyst) [1st variant of process (C)]. The amount of alkali metal alcoholate or methylate employed is advantageously close to the stoichiometric amount (at least 90% of the stoichiometric amount), relative to the compound of the formula (III) employed. The exact stoichiometric amount is preferably used; according to a preferred procedure, an alcoholic solution of the compound of the formula (III) is added gradually to an alcoholic solution of the alkali metal alcoholate. The temperature is advantageously between 10° and 50° C. At the end of the reaction, the mixture is acidified, or at least neutralized, with an acid in order to remove the alkali metal in the form of an insoluble salt. The latter is then separated off, e.g. by filtration; the compound of the formula (VIII) is obtained by evaporating off the methanol. Of course, it is possible to purify the product by the usual methods, e.g. by washing an organic solution of the compound of the formula (VIII) with water, this being followed by recrystallization if necessary.

As already stated, the reaction of an alcohol, e.g. methanol, with the compound of the formula (III) can be carried out in the presence of an acid agent or catalyst [2nd variant of process (C)], preferably a strong mineral or organic acid, e.g. hydrochloric, sulphuric or para-toluenesulphonic acid. The amount of acid catalyst employed is advantageously between 0.01 and 1 acid equivalent (which corresponds to 0.01 to 1 g.ion of H+ or mol of monoacid) per mol of compound (III). The reaction is generally carried out at a temperature above 50° C. and up to the b.p. of the reaction medium; in practice, the reaction is carried out by simply heating in the presence of the acid catalyst.

At the end of the reaction, the alcohol (if appropriate methanol) and the acid catalyst are removed, e.g. by distillation, and the product is purified by the usual methods if necessary.

In accordance with the fourth process, namely process (D), compounds of the formula (III) are prepared by reacting a mercaptan of the formula (VIII) with a derivative of an acid $R^9COOH$, preferably an acid chloride $R^9$—CO—Cl (1st variant) or an anhydride $(R^9—CO)_2O$ (2nd variant).

The reaction of an acid chloride $R^9$—CO—Cl with a mercaptan of the formula (VIII), in accordance with the 1st variant, is generally carried out in the presence of a condensation agent which is most frequently an acid acceptor (also referred to as a basic acceptor); the reaction is usually carried out in an inert organic solvent.

Inert organic solvents which may be mentioned are those indicated as desired solvents in the case of process (A).

Acid acceptors which can be used are organic bases, like tertiary amines, such as trialkylamines (e.g. triethylamine) or N-aryldialkylamines (e.g. N,N-dimethylaniline) or also pyridine and pyridine bases, or inorganic bases, such as alkali metal or alkaline earth metal carbonates or bicarbonates or sodium acetate.

The reaction is most conveniently carried out at ambient temperature, but temperatures from 5° to 60° C., preferably from 10° to 30° C., can also be used.

The proportions of the various reactants are advantageously close to (at least 90% of) the stoichiometric proportions; the 100% exact stoichiometric proportions are preferred.

The reaction is preferably carried out by mixing the acid chloride (optionally in the form of a solution) with a mixture of the compound of the formula (VIII) and the acid acceptor (this latter mixture optionally being in the form of a solution). In accordance with the most advantageous procedure, the acid chloride is added gradually to the mixture of the other two reactants.

In the course of the reaction, the acid acceptor usually gives rise, together with the acid which forms during the reaction, to a reaction by-product which can be an addition compound, e.g. a hydrochloride. The reaction by-product may be insoluble or soluble in the medium. At the end of the reaction, this reaction by-product is separated off; if this reaction by-product is insoluble, the separation can be carried out e.g. by filtration or draining; if this reaction by-product is soluble in the medium, the separation can be carried out e.g. by washing the reaction medium with water. In one way or the other, the solvent is then removed (generally by evaporation) and this leads to the compound of the formula (III); of course, the usual purification operations can also be carried out, e.g. by washing an organic solution of (III) with water or with acid aqueous solutions and/or by recrystallization.

In accordance with the 2nd variant of process (D), an acid anhydride $(R^9—CO)_2O$ is reacted with a mercaptan of the formula (VIII). In accordance with an advantageous procedure, the anhydride is prepared in situ by reacting a dehydrating agent with the acid $R^9COOH$.

The reaction is most conveniently carried out at temperatures between 10° and 120° C. in an inert organic solvent. The solvents which can be used in process (A) may be mentioned as solvents which can be used in this case.

Carbodiimides, in particular dicyclohexylcarbodiimide, may be mentioned as dehydrating agents. The amounts of dehydrating agent and of the acid $R^9COOH$ are preferably close to the stoichiometric amounts (at least 90% of the stoichiometric amounts), relative to the mercaptan of the formula (VIII).

From a practical point of view, it is also preferred to add the carbodiimide gradually to a mixture of the mercaptan of the formula (VIII) and the acid $R^9COOH$.

A substituted urea is generally formed during the reaction and this is removed at the end of the reaction by any means which is in itself known, e.g. by filtration in the case where this substituted urea is insoluble. The solvent is also removed, e.g. by evaporation, and this leads to isolation of the compound of the formula (III).

It is also possible to use other preparative processes which are particularly suitable for the products according to the invention when these products are in the form of salts.

These compounds of the formula (II) can be prepared e.g. by saponifying the corresponding esters (products of the formula (III) in which $R^7$ is an alkyl radical and $R^8$ is the hydrogen atom), this saponification being carried out e.g. with alkali metal or alkaline earth metal hydroxides. The compounds of the formula (II) can also be obtained (especially in the case where $R^8$ represents a radical $R^9$—CO—) by reacting an alkali metal hydroxide or alkaline earth metal hydroxide with a compound of the formula (II) in which $R^7$ is the hydrogen atom. It is also possible to use double decomposition reactions between a soluble salt of the formula (II) and a soluble inorganic salt of the desired cation.

The following examples, which are given without implying a limitation, illustrate the invention and show how it can be put into practice.

Examples 1 to 10 illustrate the preparation of compounds according to the invention by the various processes which can be used and are described above.

Tables I, II and III give the physical characteristics and the elementary analysis of various products according to the invention which have been prepared by analogous processes to one or other of the processes appearing in Examples 1 to 10. If the products obtained were crystalline, their m.p. has been indicated; if the products were oily, the refractive index $(n_D^{20})$, measured at 20° C. for the sodium D-line, has been indicated.

The pesticidal properties of the products in Tables I, II and III are illustrated in Examples 11 to 14; under the conditions in these examples, none of the compounds tested exhibited phytotoxicity.

In Examples 11 to 14, it is considered that a product effects a total protection against a fungal disease if the protection is at least 95%; the protection is considered to be good if it is at least 80% (but less than 95%), fairly good if it is at least 70% (but less than 80%) and average if it is at least 50% (but less than 70%).

In the present account the percentages are percentages by weight unless otherwise indicated, with the exception of those relating to the yields. In the case where the percentages are expressed relative to stoichiometric amounts, they are molar percentages.

Compounds 73 and 80 have been shown in the ionic form; it must be clearly understood that they can also be considered as being in the covalent form —COOH.

In the examples which follow, the structure of all the products obtained was verified by nuclear magnetic resonance spectrography (N.M.R.).

EXAMPLE 1

N-(2,6-Dimethylphenyl)-alanine methyl ester of the formula

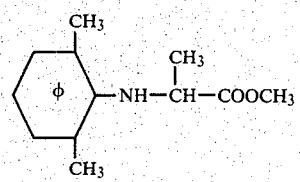

(10.35 g) is dissolved in toluene (40 cc). This solution is heated to the boil. A second solution, consisting of toluene (20 cc) and acetylthioacetyl chloride of the formula $CH_3—CO—S—CH_2—COCl$ (7.63 g), is added gradually, in the course of 10 minutes, to this solution which has thus been heated to the boil under reflux. The evolution of hydrogen chloride is observed during this operation and heating is continued until this evolution of gas ceases (i.e. for 15 minutes). The toluene is then removed by distillation under reduced pressure.

N-[(Acetylthio)-acetyl]-N-(2,6-dimethylphenyl)-alanine methyl ester, which is compound No. 1 in Table (I), is thus obtained with a yield of 100%.

Its m.p., after recrystallization from ethyl alcohol, and also the elementary analysis are indicated in Table I.

EXAMPLE 2

A solution of N-(2,6-dimethylphenyl)-alanine (19.3 g, 0.1 mol) in toluene (100 cc) is heated to the boil under reflux. A solution consisting of acetylthioacetyl chloride (15.25 g, 0.1 mol) and toluene (20 cc) is added gradually in the course of 15 minutes, whilst keeping the mixture at the boil. Boiling is then maintained for a further 15 minutes until the evolution of hydrogen chloride gas ceases. Half (by volume) of the solvents in the reaction medium is removed by distillation; the residue is cooled to 0° C.; the resulting precipitate is filtered off, washed with hexane (10 cc), drained and finally dried in vacuo (absolute pressure reduced to 27 millibars) at 20° C. N-[(Acetylthio)-acetyl]-N-(2,6-dimethylphenyl)-alanine (compound No. 80) (15.5 g; yield: 55%), the m.p. and elementary analysis of which are indicated in Table III, is thus obtained. The reaction carried out was:

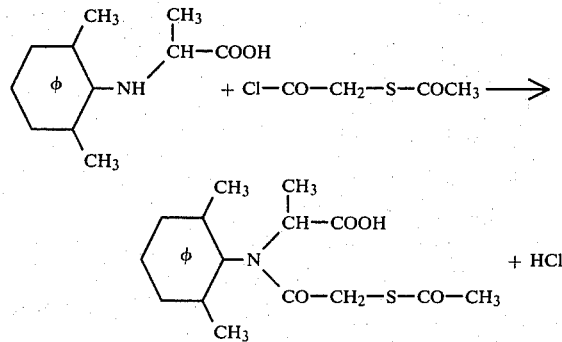

EXAMPLE 3

Mercaptoacetic acid ($CH_3COSH$) (4.18 g) is run, in the course of 30 minutes, into a suspension of sodium carbonate (2.97 g) in dimethylformamide (30 cc). When the medium has become homogeneous, N-(2,6-dimethylphenyl)-N-(chloroacetyl)-alanine methyl ester of the formula:

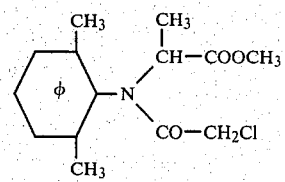

(14.17 g) is added. The mixture is heated for 2 hours at 100° C., whilst stirring. After cooling, the sodium chloride formed is removed by filtration and the dimethylformamide is removed by distillation under reduced pressure. The residual oil is dissolved in methylene chloride (30 cc) and the resulting solution is washed with water (4×10 cc); the organic solution washed in this way is dried over magnesium sulphate and filtered and the filtrate is then concentrated to dryness. The resulting oil, to which ethanol (5 cc) is added, produces a crystalline precipitate which forms slowly. N-(2,6-Dimethylphenyl)-N-[(acetylthio)-acetyl]-alanine methyl ester, which is compound No. 1 and the characteristics of which are indicated in Table (I), is thus obtained with a yield of 62%.

EXAMPLE 4

N-(2,6-Dimethylphenyl)-N-[(acetylthio)-acetyl]alanine methyl ester (compound No. 1 in Table (I)) (35 g) is dissolved in methanol (70 cc).

A solution of sodium methylate, prepared by adding sodium (2.5 g) to methanol (150 cc), is added gradually, in the course of 1 hour, at 30° C., to this first solution.

The reaction medium produced by mixing these two solutions is acidified with an aqueous solution of concentrated hydrochloric acid (10 cc). The sodium chloride formed is filtered off; the filtrate is distilled in vacuo so as to evaporate off the methanol; the residue resulting from this evaporation is dissolved in methylene chloride (50 cc); this solution is washed with water until the wash water is neutral and is then dried over sodium sulphate. The methylene chloride is then removed by evaporation; the oily residue is intimately mixed with hexane (100 cc) and this produces a crystalline precipitate consisting of N-(2,6-dimethylphenyl)-N-(mercaptoacetyl)-alanine methyl ester, which is compound No. 55 in Table (II); this table indicates the m.p. and elementary analysis of this compound. This compound was thus obtained with a yield of 82%.

EXAMPLE 5

N-(2,6-Dimethylphenyl)-N-[(acetylthio)-acetyl]alanine methyl ester (323 g, 1 mol), namely compound No. 1 in Table (I), is dissolved in methanol (one liter). A concentrated aqueous solution of hydrochloric acid (10 cc) is added and the mixture is heated at the boil under reflux for 5 hours. The methanol is removed by distillation. The oily residue is crystallized by stirring it in petroleum ether. The precipitate is filtered off and then dried under an absolute pressure reduced to 27 millibars. N-(2,6-Dimethylphenyl)-N-(mercaptoacetyl)-alanine methyl ester, which is compound No. 55 in Table (II), is obtained with a yield of 98%.

EXAMPLE 6

Triethylamine (2.5 g) and N-(2,6-dimethylphenyl)-N-(mercaptoacetyl)-alanine methyl ester of the formula

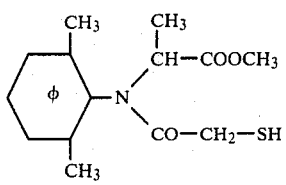

(7 g) are dissolved in toluene (40 cc).

A solution of 3,3-dimethylbutanoic acid chloride (3.6 g) in toluene (20 cc) is added gradually to this solution in the course of 20 minutes, whilst stirring continuously; the temperature rises from a value of 20° C. to a value of 30° C. during this addition. Stirring is continued for half an hour; the triethylamine hydrochloride is removed by draining; the remaining toluene solution resulting from this draining is washed with a solution of sodium bicarbonate and then with water. The toluene is removed under reduced pressure and an oil consisting of N-(2,6-dimethylphenyl)-N-[(3,3-dimethylbutanoylthio)-acetyl]-alanine methyl ester of the formula

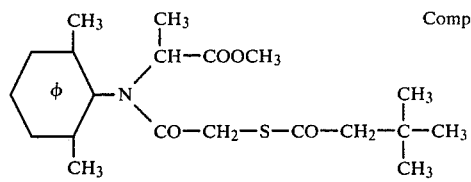

Compound No. 10 is then obtained.

This product was obtained with a yield of 84%.

The m.p. and elementary analysis are indicated in Table (I).

EXAMPLE 7

Methyl N-(2,6-dimethylphenyl)-N-(mercaptoacetyl)alaninate of the formula

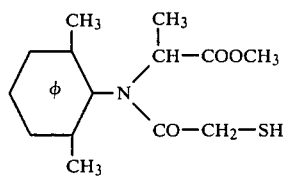

(14.05 g, 0.05 mol) and cyanoacetic acid (N≡C—CH₂—COOH) (4.25 g, 0.05 mol) are dissolved in methylene chloride (100 cc).

The mixture is stirred at 20° C. and a solution of dicyclohexylcarbodiimide (10.3 g) in methylene chloride (50 cc) is added gradually in the course of 15 minutes. The mixture is then heated at the boil under reflux for 2 hours and subsequently cooled to 0° C. The precipitate of dicyclohexylurea is filtered off, the solvent is removed by distillation, diethyl ether (50 cc) is added to the residue and the mixture is cooled to −20° C. The precipitate is filtered off and dried. Methyl N-[(cyanoacetylthio)-acetyl]-N-(2,6-dimethylphenyl)alaninate (compound No. 48) (9 g; yield 51%), the m.p. and elementary analysis of which are indicated in Table I, is obtained.

EXAMPLE 8

A solution consisting of methyl N-(2,6-dimethylphenyl)-N-(mercaptoacetyl)-alaninate (70.25 g, 0.25 mol) and of a 0.125 N aqueous solution of sodium hydroxide (200 cc) is heated at the boil under reflux for 2 hours.

It is concentrated to dryness under reduced pressure.

Sodium N-(2,6-dimethylphenyl)-N-(mercaptoacetyl)alaninate (compound No. 75) (72.3 g; yield: 100%), the m.p. and elementary analysis of which are indicated in Table (III), is thus obtained. The reaction carried out was

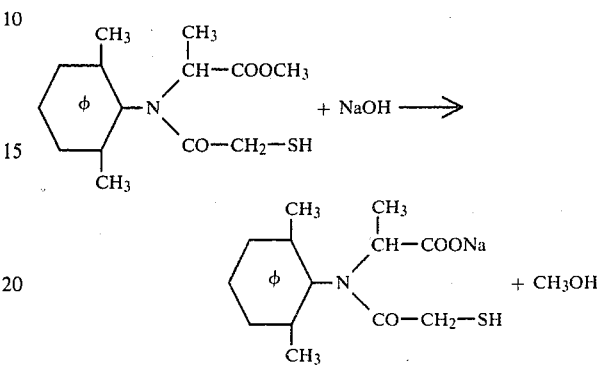

EXAMPLE 9

A suspension consisting of water (50 cc), MgO (0.4 g, 0.01 mol) and N-[(acetylthio)-acetyl]-N-(2,6-dimethylphenyl)-alanine (6.18 g, 0.02 mol) is heated at the boil under reflux (for 2 hours) until dissolution takes place. The solution is cooled to 0° C. The precipitate is filtered off, drained and then dried at 40° C. under an absolute pressure of 27 millibars and in the presence of P₂O₅.

Magnesium N-[(acetylthio)-acetyl]-N-(2,6-dimethylphenyl)-alaninate (4.6 g; yield: 72%), the m.p. and elementary analysis of which are indicated in Table (III), is obtained. The reaction carried out was

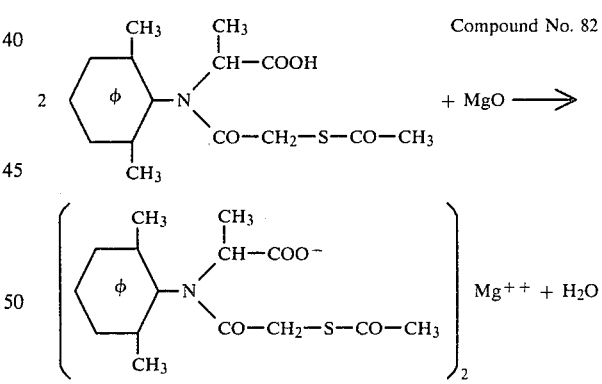

Compound No. 82

EXAMPLE 10

A solution of CuSO₄ (2.5 g, 0.01 mol) in water (50 cc) is added gradually, in the course of 15 minutes and whilst stirring, to a solution consisting of water (50 cc) and sodium N-[(acetylthio)-acetyl]-N-(2,6-dimethylphenyl)-alaninate (6.62 g, 0.02 mol). Stirring is continued for a further 15 minutes and the precipitate is filtered off, washed with water, drained and then dried at 40° C. under an absolute pressure reduced to 27 millibars and in the presence of P₂O₅.

Copper N-[(acetylthio)-acetyl]-N-(2,6-dimethylphenyl)-alaninate (compound No. 84) (5.5 g; yield 92%), the m.p. and elementary analysis of which are indicated in Table (III), is thus obtained. The reaction carried out was

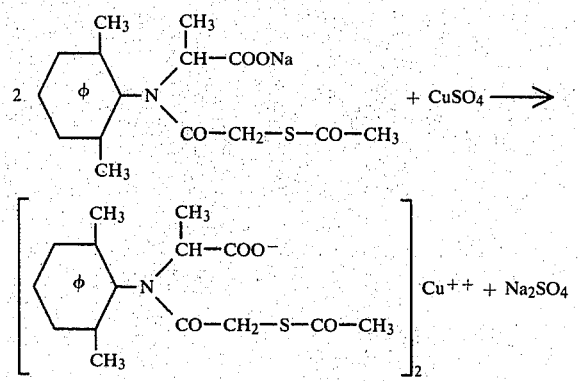

The folowing compounds can also be prepared in a similar manner to those described above: methyl N-(2,6-dimethylphenyl)-N-[(propionylthio)-acetyl]-glycinate, methyl N-(3-chloro-2,6-dimethylphenyl)-N-[(propionylthio)-acetyl]-glycinate, methyl N-(3-bromo-2,6-dimethylphenyl)-N-[(propionylthio)-acetyl]-glycinate, methyl N-[(propionylthio)-acetyl]-N-(2,3,6-trimethylphenyl)-glycinate, methyl N-(3-chloro-2,6-dimethylphenyl)-N-[(propionylthio)-acetyl]-alaninate, methyl N-(3-bromo-2,6-dimethylphenyl)-N-[(propionylthio)-acetyl]-alaninate, methyl N-[(propionylthio)-acetyl]-N-(2,3,6-trimethylphenyl)-alaninate, methyl N-[(butyrylthio)-acetyl]-N-(2,6-dimethylphenyl)-glycinate, methyl N-[(butyrylthio)-acetyl]-N-(3-chloro-2,6-dimethylphenyl)-glycinate, methyl N-(3-bromo-2,6-dimethylphenyl)-N-[(butyrylthio)-acetyl]-glycinate, methyl N-[(butyrylthio)-acetyl]-N-(2,3,6-trimethylphenyl)-glycinate, methyl N-[(butyrylthio)-acetyl]-N-(3-chloro-2,6-dimethylphenyl)-alaninate, methyl N-(3-bromo-2,6-dimethylphenyl)-N-[(butyrylthio)-acetyl]-alaninate, methyl N-[(butyrylthio)-acetyl]-N-(2,3,6-trimethylphenyl)-alaninate, methyl N-(2,6-dimethylphenyl)-N-[(isobutyrylthio)-acetyl]-glycinate, methyl N-(3-chloro-2,6-dimethylphenyl)-N-[(isobutyrylthio)-acetyl]-glycinate, methyl N-(3-bromo-2,6-dimethylphenyl)-N-[(isobutyrylthio)-acetyl]-glycinate, methyl N-[(isobutyrylthio)-acetyl]-N-(2,3,6-trimethylphenyl)-glycinate, methyl N-(3-chloro-2,6-dimethylphenyl)-N-[(isobutyrylthio)-acetyl]-alaninate, methyl N-(3-bromo-2,6-dimethylphenyl)-N-[(isobutyrylthio)-acetyl]-alaninate, methyl N-[(isobutyrylthio)-acetyl]-N-(2,3,6-trimethylphenyl)-alaninate, methyl N-(2,6-dimethylphenyl)-N-[(pentanoylthio)-acetyl]-glycinate, methyl N-(3-chloro-2,6-dimethylphenyl)-N-[(pentanoylthio)-acetyl]-glycinate, methyl N-(3-bromo-2,6-dimethylphenyl)-N-[(pentanoylthio)-acetyl]-glycinate, methyl N-[(pentanoylthio)-acetyl]-N-(2,3,6-trimethylphenyl)-glycinate, methyl N-(3-chloro-2,6-dimethylphenyl)-N-[(pentanoylthio)-acetyl]-alaninate, methyl N-(3-bromo-2,6-dimethylphenyl)-N-[(pentanoylthio)-acetyl]-alaninate, methyl N-[(pentanoylthio)-acetyl]-N-(2,3,6-trimethylphenyl)-alaninate, methyl N-(2,6-dimethylphenyl)-N-[(3-methylbutyrylthio)-acetyl]-glycinate, methyl N-(3-chloro-2,6-dimethylphenyl)-N-[(3-methylbutyrylthio)-acetyl]-glycinate, methyl N-(3-bromo-2,6-dimethylphenyl)-N-[(3-methylbutyrylthio)-acetyl]-glycinate, methyl N-[(3-methylbutyrylthio)-acetyl]-N-(2,3,6-trimethylphenyl)-glycinate, methyl N-(3-chloro-2,6-dimethylphenyl)-N-[(3-methylbutyrylthio)-acetyl]-alaninate, methyl N-(3-bromo-2,6-dimethylphenyl)-N-[(3-methylbutyrylthio)-acetyl]-alaninate, methyl N-(2,6-dimethylphenyl)-N-[(2-methylbutyrylthio)-acetyl]-glycinate, methyl N-(3-chloro-2,6-dimethylphenyl)-N-[(2-methylbutyrylthio)-acetyl]-glycinate, methyl N-(3-bromo-2,6-dimethylphenyl)-N-[(2-methylbutyrylthio)-acetyl]-glycinate, methyl N-[(2-methylbutyrylthio)-acetyl]-N-(2,3,6-trimethylphenyl)-glycinate, methyl N-(3-chloro-2,6-dimethylphenyl)-N-[(2-methylbutyrylthio)-acetyl]-alaninate, methyl N-(3-bromo-2,6-dimethylphenyl)-N-[(2-methylbutyrylthio)-acetyl]-alaninate, methyl N-[(2-methylbutyrylthio)-acetyl]-N-(2,3,6-trimethylphenyl)-alaninate, methyl N-[(3-methylbutyrylthio)-acetyl]-N-(2,3,6-trimethylphenyl)-alaninate, methyl N-(2,6-dimethylphenyl)-N-[(2,2-dimethylpropionylthio)-acetyl]-glycinate, methyl N-(3-chloro-2,6-dimethylphenyl)-N-[(2,2-dimethylpropionylthio)-acetyl]-glycinate, methyl N-(3-bromo-2,6-dimethylphenyl)-N-[(2,2-dimethylpropionylthio)-acetyl]-glycinate, methyl N-[(2,2-dimethylpropionylthio)-acetyl]-N-(2,3,6-trimethylphenyl)-glycinate, methyl N-(3-chloro-2,6-dimethylphenyl)-N-[(2,2-dimethylpropionylthio)-acetyl]-alaninate, methyl N-(3-bromo-2,6-dimethylphenyl)-N-[(2,2-dimethylpropionylthio)-acetyl]-alaninate, methyl N-[(2,2-dimethylpropionylthio)-acetyl]-N-(2,3,6-trimethylphenyl)-alaninate, methyl N-(2,6-dimethylphenyl)-N-[(hexanoylthio)-acetyl]-glycinate, methyl N-(3-chloro-2,6-dimethylphenyl)-N-[(hexanoylthio)-acetyl]-glycinate, methyl N-(3-bromo-2,6-dimethylphenyl)-N-[(hexanoylthio)-acetyl]-glycinate, methyl N-[(hexanoylthio)-acetyl]-N-(2,3,6-trimethylphenyl)-glycinate, methyl N-(3-chloro-2,6-dimethylphenyl)-N-[(hexanoylthio)-acetyl]-alaninate, methyl N-(3-bromo-2,6-dimethylphenyl)-N-[(hexanoylthio)-acetyl]-alaninate, methyl N-[(hexanoylthio)-acetyl]-N-(2,3,6-trimethylphenyl)-alaninate, methyl N-[(3,3-dimethylbutyrylthio)-acetyl]-N-(2,6-dimethylphenyl)-glycinate, methyl N-(3-chloro-2,6-dimethylphenyl)-N-[(3,3-dimethylbutyrylthio)-acetyl]-glycinate, methyl N-(3-bromo-2,6-dimethylphenyl)-N-[(3,3-dimethylbutyrylthio)-acetyl]-glycinate, methyl N-[(3,3-dimethylbutyrylthio)-acetyl]-N-(2,3,6-trimethylphenyl)-glycinate, methyl N-(3-chloro-2,6-dimethylphenyl)-N-[(3,3-dimethylbutyrylthio)-acetyl]-alaninate, methyl N-(3-bromo-2,6-dimethylphenyl)-N-[(3,3-dimethylbutyrylthio)-acetyl]-alaninate, methyl N-[(3,3-dimethylbutyrylthio)-acetyl]-N-(2,3,6-trimethylphenyl)-alaninate, methyl N-(2,6-dimethylphenyl)-N-[(2-ethylbutyrylthio)-acetyl]-glycinate, methyl N-(3-chloro-2,6-dimethylphenyl)-N-[(2-ethylbutyrylthio)-acetyl]-glycinate, methyl N-(3-bromo-2,6-dimethylphenyl)-N-[(2-ethylbutyrylthio)-acetyl]-glycinate, methyl N-[(2-ethylbutyrylthio)-acetyl]-N-(2,3,6-trimethylphenyl)-glycinate, methyl N-(3-chloro-2,6-dimethylphenyl)-N-[(2-ethylbutyrylthio)-acetyl]-alaninate, methyl N-(3-bromo-2,6-dimethylphenyl)-N-[(2-ethylbutyrylthio)-acetyl]-alaninate, methyl N-[(2-ethylbutyrylthio)-acetyl]-N-(2,3,6-trimethylphenyl)-alaninate, methyl N-(2,6-dimethylphenyl)-N-[(heptanoylthio)-acetyl]-glycinate, methyl N-(3-chloro-2,6-dimethylphenyl)-N-[(heptanoylthio)-acetyl]-glycinate, methyl N-(3-bromo-2,6-dimethylphenyl)-N-[(heptanoylthio)-acetyl]-glycinate, methyl N-[(heptanoylthio)-acetyl]-N-(2,3,6-trimethylphenyl)-glycinate, methyl N-(3-chloro-2,6-dimethylphenyl)-N-[(heptanoylthio)-acetyl]-alaninate, methyl N-(3-bromo-2,6-dimethylphenyl)-N-[(heptanoylthio)-acetyl]-alaninate, methyl N-[(heptanoylthio)-acetyl]-N-(2,3,6-trimethylphenyl)-alaninate, methyl N-(2,6-dimethylphenyl)-N-[(2-ethylhexanoylthio)-acetyl]-glycinate, methyl N-(3-chloro-2,6-dimethylphenyl)-N-[(2-ethylhexanoylthio)-acetyl]-glycinate, methyl N-(3-bromo-2,6-dimethylphenyl)-N-[(2-ethylhexanoylthio)-acetyl]-glycinate, methyl N-[(2-ethylhexanoylthio)-acetyl]-N-(2,3,6-trimethylphenyl)-glycinate, methyl N-(3-chloro-2,6-dimethylphenyl)-N-[(2-ethylhexanoylthio)-acetyl]-alaninate, methyl N-(3-bromo-2,6-dimethylphenyl)-N-[(2-ethylhexanoylthio)-acetyl]-alaninate, methyl N-[(2-ethylhexanoylthio)-acetyl]-N-(2,3,6-trimethylphenyl)-alaninate, methyl N-(2,6-dimethylphenyl)-N-[(octanoylthio)-acetyl]-glycinate, methyl N-(3-chloro-2,6-dimethylphenyl)-N-[(octanoylthio)-acetyl]-glycinate, methyl N-(3-bromo-2,6-dimethylphenyl)-N-[(octanoylthio)-acetyl]-glycinate, methyl N-[(octanoylthio)-acetyl]-N-(2,3,6-trimethylphenyl)-glycinate, methyl N-(3-chloro-2,6-dimethylphenyl)-N-[(octanoylthio)-acetyl]-alaninate, methyl N-(3-bromo-2,6-dimethylphenyl)-N-[(octanoylthio)-acetyl]-alaninate, methyl N-[(octanoylthio)-acetyl]-N-(2,3,6-trimethylphenyl)-alaninate, methyl N-(2,6-dimethylphenyl)-N-[(nonanoylthio)-acetyl]-glycinate, methyl N-(3-chloro-2,6-dimethylphenyl)-N-[(nonanoylthio)-acetyl]-glycinate, methyl N-(3-bromo-2,6-dimethylphenyl)-N-[(nonanoylthio)-acetyl]-glycinate, methyl N-[(nonanoylthio)-acetyl]-N-(2,3,6-trimethylphenyl)-glycinate, methyl N-(3-chloro-2,6-dimethylphenyl)-N-[(nonanoylthio)-acetyl]-alaninate, methyl N-(3-bromo-2,6-dimethylphenyl)-N-[(nonanoylthio)-acetyl]-alaninate, methyl N-[(nonanoylthio)-acetyl]-N-[2,3,6-trimethylphenyl)-alaninate, methyl N-(2,6-dimethylphenyl)-N-[(decanoylthio)-acetyl]-glycinate, methyl N-(3-chloro-2,6-dimethylphenyl)-N-[(decanoylthio)-acetyl]-glycinate, methyl N-(3-bromo-2,6-dimethylphenyl)-N-[(decanoylthio)-acetyl]-glycinate, methyl N-[(decanoylthio)-acetyl]-N-(2,3,6-trimethylphenyl)-glycinate, methyl N-(3-chloro-2,6-dimethylphenyl)-N-[(decanoylthio)-acetyl]-alaninate, methyl N-(3-bromo-2,6-dimethylphenyl)-N-[(decanoylthio)-acetyl]-alaninate, methyl N-[(decanoylthio)-acetyl]-N-(2,3,6-trimethylphenyl)-alaninate, methyl N-(2,6-dimethylphenyl)-N-[(undecanoylthio)-acetyl]-glycinate, methyl N-(3-chloro-2,6-dimethylphenyl)-N-[(undecanoylthio)-acetyl]-glycinate, methyl N-(3-bromo-2,6-dimethylphenyl)-N-[(undecanoylthio)-acetyl]-glycinate, methyl N-(2,3,6-trimethylphenyl)-N-[(undecanoylthio)-acetyl]-glycinate, methyl N-(3-chloro-2,6-dimethylphenyl)-N-[(undecanoylthio)-acetyl]-alaninate, methyl N-(3-bromo-2,6-dimethylphenyl)-N-[(undecanoylthio)-acetyl]-alaninate, methyl N-(2,3,6-trimethylphenyl)-N-[(undecanoylthio)-acetyl]-alaninate, methyl N-(2,6-dimethylphenyl)-N-[(dodecanoylthio)-acetyl]-glycinate, methyl N-(3-chloro-2,6-dimethylphenyl)-N-[(dodecanoylthio)-acetyl]-glycinate, methyl N-(3-bromo-2,6-dimethylphenyl)-N-[(dodecanoylthio)-acetyl]-glycinate, methyl N-[(dodecanoylthio)-acetyl]-N-(2,3,6-trimethylphenyl)-glycinate, methyl N-(3-chloro-2,6-dimethylphenyl)-N-[(dodecanoylthio)-acetyl]-alaninate, methyl N-(3-bromo-2,6-dimethylphenyl)-N-[(dodecanoylthio)-acetyl]-alaninate, methyl N-[(dodecanoylthio)-acetyl]-N-(2,3,6-trimethylphenyl)-alaninate, methyl N-(2,6-dimethylphenyl)-N-[(tetradecanoylthio)-acetyl]-glycinate, methyl N-(3-chloro-2,6-dimethylphenyl)-N-[(tetradecanoylthio)-acetyl]-glycinate, methyl N-(3-bromo-2,6-dimethylphenyl)-N-[(tetradecanoylthio)-acetyl]-glycinate, methyl N-[(tetradecanoylthio)-acetyl]-N-(2,3,6-trimethylphenyl)-glycinate, methyl N-(3-chloro-2,6-dimethylphenyl)-N-[(tetradecanoylthio)-acetyl]-alaninate, methyl N-(3-bromo-2,6-dimethylphenyl)-N-[(tetradecanoylthio)-acetyl]-alaninate, methyl N-[(tetradecanoylthio)-acetyl]-N-(2,3,6-trimethylphenyl)-alaninate, methyl N-(2,6-dimethylphenyl)-N-[(hexadecanoylthio)-acetyl]-glycinate, methyl N-(3-chloro-2,6-dimethylphenyl)-N-[(hexadecanoylthio)-acetyl]-glycinate, methyl N-(3-bromo-2,6-dimethylphenyl)-N-[(hexadecanoylthio)-acetyl]-glycinate, methyl N-[(hexadecanoylthio)-acetyl]-N-(2,3,6-trimethylphenyl)-glycinate, methyl N-(3-chloro-2,6-dimethylphenyl)-N-[(hexadecanoylthio)-acetyl]-alaninate, methyl N-(3-bromo-2,6-dimethylphenyl)-N-[(hexadecanoylthio)-acetyl]-alaninate, methyl N-[(hexadecanoylthio)-acetyl]-N-(2,3,6-trimethylphenyl)-alaninate, methyl N-(2,6-dimethylphenyl)-N-[(octadecanoylthio)-acetyl]-glycinate, methyl N-(3-chloro-2,6-dimethylphenyl)-N-[(octadecanoylthio)-acetyl]-glycinate, methyl N-(3-bromo-2,6-dimethylphenyl)-N-[(octadecanoylthio)-acetyl]-glycinate, methyl N-[(octadecanoylthio)-acetyl]-N-(2,3,6-trimethylphenyl)-glycinate, methyl N-(3-chloro-2,6-dimethylphenyl)-N-[(octadecanoylthio)-acetyl]-alaninate, methyl N-(3-bromo-2,6-dimethylphenyl)-N-[(octadecanoylthio)-acetyl]-alaninate, methyl N-[(octadecanoylthio)-acetyl]-N-(2,3,6-trimethylphenyl)-alaninate, methyl N-[(cyclohexanecarbonylthio)-acetyl]-N-(2,6-dimethylphenyl)-glycinate, methyl N-(3-chloro-2,6-dimethylphenyl)-N-[(cyclohexanecarbonylthio)-acetyl]-glycinate, methyl N-(3-bromo-2,6-dimethylphenyl)-N-[(cyclohexanecarbonylthio)-acetyl]-glycinate, methyl N-[(cyclohexanecarbonylthio)-acetyl]-N-(2,3,6-trimethylphenyl)-glycinate, methyl N-(3-chloro-2,6-dimethylphenyl)-N-[(cyclohexylcarbonylthio)-acetyl]-alaninate, methyl N-(3-bromo-2,6-dimethylphenyl)-N-[(cyclohexylcarbonylthio)-acetyl]-alaninate, methyl N-[(cyclohexylcarbonylthio)-acetyl]-N-(2,3,6-trimethylphenyl)-alaninate, methyl N-[(cyclopentylcarbonylthio)-acetyl]-N-(2,6-dimethylphenyl)-glycinate, methyl N-(3-chloro-2,6-dimethylphenyl)-N-[(cyclopentylcarbonylthio)-acetyl]-glycinate, methyl N-(3-bromo-2,6-dimethylphenyl)-N-[(cyclopentylcarbonylthio)-acetyl]-glycinate, methyl N-[(cyclopentylcarbonylthio)-acetyl]-N-(2,3,6-trimethylphenyl)-glycinate, methyl N-(3-chloro-2,6-dimethylphenyl)-N-[(cyclopentylcarbonylthio)-acetyl]-alaninate, methyl N-(3-bromo-2,6-dimethylphenyl)-N-[(cyclopentylcarbonylthio)-acetyl]-alaninate, methyl N-[(cyclopentylcarbonylthio)-acetyl]-N-(2,3,6-trimethylphenyl)-alaninate, methyl N-[(3,3-dimethylacryloylthio)-acetyl]-N-(2,6-dimethylphenyl)-glycinate, methyl N-(3-chloro-2,6-dimethylphenyl)-N-[(3,3-dimethylacryloylthio)-acetyl]-glycinate, methyl N-(3-bromo-2,6-dimethylphenyl)-N-[(3,3-dimethylacryloylthio)-acetyl]-glycinate, methyl N-[(3,3-dimethylacryloylthio)-acetyl]-N-(2,3,6-trimethylphenyl)-glycinate, methyl N-(3-chloro-2,6-dimethylphenyl)-N-[(3,3-dimethylacryloylthio)-acetyl]-alaninate, methyl N-(3-bromo-2,6-dimethylphenyl)-N-[(3,3-dimethylacryloylthio)-acetyl]-alaninate, methyl N-[(3,3-dimethacryloylthio)-acetyl]-N-(2,3,6-trimethylphenyl)-alaninate, methyl N-[(benzoylthio)-acetyl]-N-(2,6-dimethylphenyl)-glycinate, methyl N-[(benzoylthio)-acetyl]-N-(3-chloro-2,6-dimethylphenyl)-glycinate, methyl N-[(benzoylthio)-acetyl]-N-(3-bromo-2,6-dimethylphenyl)-glycinate, methyl N-[(benzoylthio)-acetyl]-N-[(2,3,6-trimethylphenyl)-glycinate, methyl N-[(benzoylthio)-acetyl]-N-(3-chloro-2,6-dimethylphenyl)-alaninate, methyl N-[(benzoylthio)-acetyl]-N-(3-bromo-2,6-dimethylphenyl)-alaninate, methyl N-[(benzoylthio)-acetyl]-N-(2,3,6-trimethylphenyl)-alaninate, methyl N-(2,6-dimethylphenyl)-N-[(methoxyacetylthio)-acetyl]-glycinate, methyl N-(3-chloro-2,6-dimethylphenyl)-N-[(methoxyacetylthio)-acetyl]-glycinate, methyl N-(3-bromo-2,6-dimethylphenyl)-N-[(methoxyacetylthio)-acetyl]-glycinate, methyl N-[(methoxyacetylthio)-acetyl]-N-(2,3,6-trimethylphenyl)-glycinate, methyl N-(3-chloro-2,6-dimethylphenyl)-N-[(methoxyacetylthio)-acetyl]-alaninate, methyl N-(3-bromo-2,6-dimethylphenyl)-N-[(methoxyacetylthio)-acetyl]-alaninate, methyl N-[(methoxyacetylthio)-acetyl]-N-(2,3,6-trimethylphenyl)-alaninate, methyl N-(2,6-dimethylphenyl)-N-[(2-furanylcarbonylthio)-acetyl]-glycinate, methyl N-(3-chloro-2,6-dimethylphenyl)-N-[(2-furanylcarbonylthio)-acetyl]-glycinate, methyl N-(3-bromo-2,6-dimethylphenyl)-N-[(2-furanylcarbonylthio)-acetyl]-glycinate, methyl N-[(2-furanylcarbonylthio)-acetyl]-N-(2,3,6-trimethylphenyl)-glycinate, methyl N-(3-chloro-2,6-dimethylphenyl)-N-[(2-furanylcarbonylthio)-acetyl]-alaninate, methyl N-(3-bromo-2,6-dimethylphenyl)-N-[(2-furanylcarbonylthio)-acetyl]-alaninate, methyl N-[(2-furanylcarbonylthio)-acetyl]-N-(2,3,6-trimethylphenyl)-alaninate, methyl N-(2,6-dimethylphenyl)-N-[(2-thienylcarbonylthio)-acetyl]-glycinate, methyl N-(3-chloro-2,6-dimethylphenyl)-N-[(2-thienylcarbonylthio)-acetyl]-glycinate, methyl N-(3-bromo-2,6-dimethylphenyl)-N-[(2-thienylcarbonylthio)-acetyl]-glycinate, methyl N-[(2-thienylcarbonylthio)-acetyl]-N-(2,3,6-trimethylphenyl)-glycinate, methyl N-(3-chloro-2,6-dimethylphenyl)-N-[(2-thienylcarbonylthio)-acetyl]-alaninate, methyl N-(3-bromo-2,6-dimethylphenyl)-N-[(2-thienylcarbonylthio)-acetyl]-alaninate, methyl N-[(2-thienylcarbonylthio)-acetyl]-N-(2,3,6-trimethylphenyl)-alaninate, methyl N-[(acetylthio)-acetyl]-N-(3-chloro-2,6-dimethylphenyl)-glycinate, methyl N-[(acetylthio)-acetyl]-N-(3-bromo-2,6-dimethylphenyl)-glycinate, methyl N-[(acetylthio)-acetyl]-N-(2,3,6-trimethylphenyl)-glycinate, methyl N-[(acetylthio)-acetyl]-N-(3-bromo-2,6-dimethylphenyl)-alaninate, methyl N-[(acetylthio)-acetyl]-N-(2,3,6-trimethylphenyl)-alaninate, methyl N-(3-chloro-2,6-dimethylphenyl)-N-(mercaptoacetyl)-glycinate, methyl N-(3-bromo-2,6-dimethylphenyl)-N-(mercaptoacetyl)-glycinate, methyl N-(mercaptoacetyl)-N-(2,3,6-trimethylphenyl)-glycinate, methyl N-(3-chloro-2,6-dimethylphenyl)-N-(mercaptoacetyl)-alaninate, methyl N-(3-bromo-2,6-dimethylphenyl)-N-(mercaptoacetyl)-alaninate and methyl N-(mercaptoacetyl)-N-(2,3,6-trimethylphenyl)-alaninate.

TABLE I

Compounds of the formula $$\phi\text{-}N\begin{pmatrix}CH(CH_3)\text{-}COOCH_3\\ CO\text{-}CH_2\text{-}S\text{-}CO\text{-}R^9\end{pmatrix}$$

where $\phi$ is 2,6-dimethylphenyl (CH$_3$ groups at 2,6 positions).

| Compound No. | $R^9$ | Physical characteristics M.p. in °C. | $n_D^{20}$ | Values calculated, % C | H | N | S | Values found, % C | H | N | S |
|---|---|---|---|---|---|---|---|---|---|---|---|
| 1 | CH$_3$— | 52 | | 59.42 | 6.54 | 4.33 | | 59.48 | 6.60 | 4.23 | |
| 2 | C$_2$H$_5$— | 57 | | | | | | | | | |
| 3 | n-C$_3$H$_7$— | | 1.5335 | | | | | | | | |
| 4 | (CH$_3$)$_2$CH— | | 1.5332 | 61.54 | 7.12 | 3.99 | 9.12 | 61.60 | 7.16 | 3.97 | 9.13 |
| 5 | n-C$_4$H$_9$— | | 1.531 | 62.47 | 7.40 | 3.84 | 8.77 | 62.53 | 7.52 | 3.90 | 8.53 |
| 6 | (CH$_3$)$_2$CH—CH$_2$— | | 1.529 | 62.44 | 7.45 | 3.8 | 8.77 | 62.9 | 7.40 | 3.53 | 8.67 |
| 7 | CH$_3$—CH(C$_2$H$_5$)— | | 1.5400 | 62.44 | 7.45 | 3.83 | | 61.46 | 7.30 | 3.97 | |
| 8 | (CH$_3$)$_3$C— | | 1.5299 | 62.47 | 7.39 | 3.84 | 8.77 | 62.55 | 7.39 | 3.74 | 8.71 |
| 9 | n-C$_5$H$_{11}$— | | 1.526 | 63.30 | 7.70 | 3.69 | 8.45 | 63.35 | 7.58 | 3.71 | 8.15 |
| 10 | (CH$_3$)$_3$C—CH$_2$— | 68 | | 63.22 | 7.65 | 3.69 | 8.44 | 63.38 | 7.58 | 3.67 | 8.36 |
| 11 | (C$_2$H$_5$)$_2$—CH— | | 1.518 | 63.32 | 7.65 | 3.69 | 8.44 | 63.81 | 8.11 | 3.51 | 7.05 |
| 12 | n-C$_6$H$_{13}$— | | 1.525 | 64.12 | 7.89 | 3.56 | 8.14 | 63.44 | 7.52 | 3.60 | 8.28 |
| 13 | n-C$_7$H$_{15}$— | | 1.514 | 64.86 | 8.11 | 3.44 | 7.86 | 64.52 | 8.17 | 3.27 | 6.66 |
| 14 | n-C$_4$H$_9$—CH(C$_2$H$_5$)— | | 1.5175 | 65.51 | 8.19 | 3.47 | 7.94 | 64.10 | 7.94 | 3.40 | 8.06 |
| 15 | n-C$_8$H$_{17}$— | | 1.514 | | | | | | | | |
| 16 | n-C$_9$H$_{19}$— | | | | | | | | | | |
| 17 | n-C$_{10}$H$_{21}$— | | 1.509 | 66.82 | 8.7 | 3.12 | 7.13 | 67.58 | 9.3 | 3.75 | 6.1 |
| 18 | n-C$_{11}$H$_{23}$— | 35 | | 67.35 | 8.91 | 3.02 | 6.92 | 67.75 | 9.25 | 2.90 | 6.87 |
| 19 | n-C$_{13}$H$_{27}$— | 37.5 | | 68.43 | 9.16 | 2.85 | 6.52 | 68.33 | 9.27 | 2.90 | 6.66 |
| 20 | n-C$_{16}$H$_{33}$— | | | | | | | | | | |
| 21 | n-C$_{17}$H$_{35}$— | 38 | | 70.20 | 9.67 | 2.56 | 5.85 | 69.78 | 9.73 | 3.07 | 5.04 |
| 22 | cyclopropyl (CH$_2$—CH—CH$_2$) | 107 | | | | | | | | | |
| 23 | cyclopentyl (CH$_2$—CH$_2$—CH—CH$_2$—CH$_2$) | 45 | | | | | | | | | |

TABLE I-continued

Compounds of the formula $$\phi\text{-cyclohexyl(2,6-diCH}_3\text{)-N(CH(CH}_3\text{)COOCH}_3\text{)(CO-CH}_2\text{-S-CO-R}^9\text{)}$$

| Compound No. | R⁹ | M.p. in °C. | $n_D^{20}$ | C calc. | H calc. | N calc. | S calc. | C found | H found | N found | S found |
|---|---|---|---|---|---|---|---|---|---|---|---|
| 24 | cyclohexyl | 90.5 | | 64.42 | 7.47 | 3.58 | 8.19 | 64.10 | 7.63 | 3.55 | 8.31 |
| 25 | (CH₃)₂C=CH— | 86 | | 62.79 | 6.93 | 3.85 | 8.82 | 62.67 | 6.91 | 3.67 | 8.97 |
| 26 | C₆H₅—CH=CH— | 150.5 | | 67.13 | 6.12 | 3.40 | 7.79 | 66.92 | 6.34 | 3.36 | 7.78 |
| 27 | CH₂=CH—(CH₂)₇— | | 1.515 | 67.11 | 8.28 | 3.13 | 7.16 | 66.50 | 8.20 | 3.00 | 7.50 |
| 28 | CH₃(CH₂)₇—CH=CH—(CH₂)₇— | | 1.515 | 70.42 | 9.42 | 2.57 | 5.87 | 68.9 | 9.18 | 2.48 | 5.80 |
| 29 | phenyl | 95 | | 65.43 | 6.01 | 3.63 | 8.32 | 65.32 | 6.14 | 3.56 | 8.75 |
| 30 | phenyl-CH₂— | 76.3 | | 66.17 | 6.27 | 3.51 | 8.02 | 65.95 | 6.28 | 3.51 | 8.36 |
| 31 | methylnaphthyl | 152.3 | | 68.97 | 5.75 | 3.22 | 7.36 | 68.75 | 5.82 | 3.19 | 7.40 |
| 32 | 2-CH₃-phenyl | 79.2 | | 66.17 | 6.27 | 3.51 | 8.02 | 65.98 | 6.37 | 3.45 | 8.00 |
| 33 | 2-Cl-phenyl | 90.1 | | 60.07 | 5.24 | 3.34 | 7.63 | 60.03 | 5.26 | 3.31 | 7.70 |
| 34 | Cl-phenyl-CH(CH(CH₃)₂)— | 75 | | | | | | | | | |
| 35 | Cl—CH₂— | | 1.5553 | 53.71 | 5.59 | 3.92 | 8.95 | 55.07 | 5.72 | 3.95 | 8.95 |
| 36 | Cl₂CH— | 79 | | 48.98 | 4.85 | 3.57 | 8.16 | 50.03 | 5.11 | 3.68 | 8.33 |
| 37 | Cl₃C— | | 1.555 | | | | | | | | |
| 38 | CH₃O—CH₂— | 68.6 | | 57.79 | 6.52 | 3.97 | 9.06 | 58.18 | 6.50 | 3.97 | 9.73 |
| 39 | CH₃—CHCl— | 53 | | 54.91 | 5.92 | 3.77 | 8.61 | 55.18 | 6.38 | 3.29 | 7.28 |
| 40 | Cl—(CH₂)₃— | | 1.541 | 56.03 | 6.23 | 3.63 | 8.3 | 54.03 | 6.04 | 3.47 | 8.31 |
| 41 | CH₃—S—CH₂— | | 1.562 | | | | | | | | |
| 42 | furyl | 95 | | 60.78 | 5.64 | 3.73 | 8.54 | 60.92 | 5.59 | 3.77 | 8.64 |
| 43 | thienyl | 112 | | 58.29 | 5.41 | 3.58 | | 58.38 | 5.34 | 3.78 | |
| 44 | methylpyridyl | 108 | | 62.3 | 5.7 | 7.3 | 8.2 | 61.8 | 6.9 | 6.9 | 8.66 |
| 45 | pyridyl | 103 | | | | | | | | | |
| 46 | thienyl-CH₂— | | | | | | | | | | |
| 47 | trichlorothienyl | 156.5 | | 46.15 | 3.64 | 2.9 | 13.3 | 46.25 | 3.56 | 2.7 | 13.30 |
| 48 | N≡C—CH₂— | 128 | | 58.62 | 5.75 | 8.05 | | 58.83 | 5.90 | 7.90 | |
| 49 | C₂H₅—O—CO—CH₂— | 66 | | 57.72 | 6.32 | 3.54 | | 57.69 | 6.44 | 3.56 | |
| 50 | CH₃—CO—CH₂— | 78 | | 59.18 | 6.30 | 3.83 | | 59.04 | 6.26 | 3.88 | |
| 51 | C₂H₅—O—CO— | 55.4 | | 56.69 | 6.03 | 3.67 | | 56.75 | 6.08 | 3.76 | |
| 52 | C₂H₅—O—CO—CH=CH— | 70.3 | | 58.97 | 6.14 | 3.44 | | 58.97 | 6.33 | 3.41 | |

TABLE I-continued

Compounds of the formula

| Compound No. | R⁹ | Physical characteristics M.p. in °C. | $n_D^{20}$ | Elementary analysis Values calculated, % C | H | N | S | Values found, % C | H | N | S |
|---|---|---|---|---|---|---|---|---|---|---|---|
| 53 | CH₃—CO—NH—CH₂— (trans) | 133 | | 56.84 | 6.31 | 7.36 | | 54.9 | 6.35 | 7.20 | |
| 54 | CH₃—CO—O—⌬-CH₃ (φ) | 112 | | | | | | | | | |

TABLE II

Compounds of the formula $$\underset{R^4\quad R^5}{\overset{R^2\quad R^1}{\phi}}\!-\!N\!\!\begin{array}{c}CH(R^6)-CO-O-R^7\\ CO-CH_2-S-R^8\end{array}$$

| Compound No. | R¹— | R²— | R³— | R⁴— | R⁵— | R⁶— | R⁷— | R⁸— |
|---|---|---|---|---|---|---|---|---|
| 55 | CH₃— | H— | H— | H— | CH₃— | CH₃— | CH₃— | H— |
| 56 | CH₃— | Cl— | CH₃— | H— | CH₃— | CH₃— | CH₃— | CH₃—CO— |
| 57 | Cl— | H— | CH₃— | H— | H— | CH₃— | CH₃— | CH₃—CO— |
| 58 | (CH₃)₂CH— | H— | H— | H— | H— | CH₃— | CH₃— | CH₃—CO— |
| 59 | C₂H₅— | H— | H— | H— | C₂H₅— | CH₃— | CH₃— | CH₃—CO— |
| 60 | CH₃O— | H— | H— | H— | H— | CH₃— | CH₃— | CH₃—CO— |
| 61 | Br— | H— | H— | H— | H— | CH₃— | CH₃— | CH₃—CO— |
| 62 | CH₃— | Br— | CH₃— | H— | CH₃— | CH₃ | CH₃— | CH₃CO— |
| 63 | H— | Cl— | H— | H— | CH₃O— | CH₃— | CH₃— | CH₃CO— |
| 64 | CH₃— | H— | CH₃— | H— | CH₃— | CH₃— | CH₃— | CH₃CO— |
| 65 | Cl— | H— | H— | H— | CH₃— | CH₃— | CH₃— | CH₃CO— |
| 66 | CH₃— | Cl— | H— | H— | CH₃— | CH₃— | CH₃— | CH₃CO— |
| 67 | CH₃— | H— | H— | H— | CH₃— | H— | CH₃— | H— |
| 68 | CH₃— | H— | H— | H— | CH₃— | H— | CH₃— | CH₃CO— |
| 69 | CH₃— | H— | H— | H— | CH₃— | CH₃— | (CH₃)₂CH— | CH₃CO— |
| 70 | CH₃— | H— | H— | H— | CH₃— | CH₃— | (CH₃)₂CH—CH₂— | CH₃CO— |
| 71 | CH₃— | H— | H— | H— | CH₃— | CH₃— | n-C₆H₁₃— | CH₃CO— |
| 72 | CH₃— | H— | H— | H— | CH₃— | CH₃— | n-C₁₂H₂₅— | CH₃CO— |
| 85 | CH₃— | Br | H— | H— | CH₃— | CH₃— | CH₃— | CH₃CO— |
| 86 | CH₃— | Br | H— | H— | CH₃— | CH₃— | CH₃— | H— |
| 87 | CH₃— | Br | H— | H— | CH₃— | CH₃— | CH₃— | n-C₉H₁₉—CO— |
| 88 | CH₃— | Cl | H— | H— | CH₃— | CH₃— | CH₃— | H— |
| 89 | CH₃— | Cl | H— | H— | CH₃— | CH₃— | CH₃— | n-C₉H₁₉—CO— |
| 90 | CH₃— | Cl | H— | H— | CH₃— | H— | CH₃— | CH₃CO— |
| 91 | CH₃— | Cl— | H— | H— | CH₃— | H— | CH₃— | H— |
| 92 | CH₃— | Cl— | H— | H— | CH₃— | H— | CH₃— | n-C₉H₁₉—CO— |
| 93 | CH₃— | H— | H— | H— | CH₃— | H— | CH₃— | n-C₉H₁₉—CO— |

Physical characteristics

| Compound No. | M.p. in °C. | $n_D^{20}$ | Elementary analysis 1st line: values calculated, % 2nd line: values found, % C | H | N | S |
|---|---|---|---|---|---|---|
| 55 | 64 | | 59.76 | 6.81 | 4.98 | 11.37 |
| | | | 59.76 | 6.75 | 4.63 | 11.35 |
| 56 | | 1.553 | 54.91 | 5.96 | 3.77 | 8.62 |
| | | | 54.70 | 6.11 | 3.60 | 8.70 |
| 57 | | 1.547 | 52.40 | 5.28 | 4.07 | 9.33 |
| | | | 52.80 | 5.50 | 4.10 | 8.80 |
| 58 | | 1.535 | | | | |
| 59 | | 1.537 | 61.51 | 7.17 | 3.99 | 9.12 |
| | | | 61.75 | 7.35 | 3.95 | 9.0 |
| 60 | 48.5 | | 55.37 | 5.89 | 4.30 | 9.85 |

TABLE II-continued
Compounds of the formula
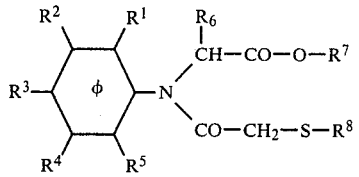
| | | | | | | | |
|---|---|---|---|---|---|---|---|
| | | | | 55.21 | 6.02 | 4.28 | 9.75 |
| 61 | | 93 | | 44.93 | 4.31 | 3.74 | 8.57 |
| | | | | 44.94 | 4.38 | 3.67 | 8.32 |
| 62 | | | | 49.04 | 5.29 | 3.37 | 7.69 |
| | | | | 49.15 | 5.55 | 3.20 | 7.91 |
| 63 | | 68.5 | | 50.07 | 5.04 | 3.89 | 8.91 |
| | | | | 50.17 | 5.17 | 3.82 | 8.86 |
| 64 | | | 1.541 | 60.90 | 6.87 | 4.15 | 9.50 |
| | | | | 60.40 | 6.90 | 4.08 | 9.40 |
| 65 | | | 1.548 | | | | |
| 66 | | | 1.551 | 53.80 | 5.60 | 9.90 | 8.90 |
| | | | | 52.63 | 5.52 | 9.86 | 9.4 |
| 67 | | 59.3 | | 58.43 | 6.37 | 5.24 | 11.99 |
| | | | | 58.56 | 6.52 | 5.22 | 12.23 |
| 68 | | 69 | | 58.25 | 6.15 | 4.53 | 10.36 |
| | | | | 58.35 | 6.25 | 4.53 | 10.36 |
| 69 | | | 1.5235 | 61.54 | 7.12 | 3.99 | 9.12 |
| | | | | 60.01 | 7.08 | 4.87 | 9.44 |
| 70 | | | 1.527 | 62.47 | 7.40 | 3.84 | 8.77 |
| | | | | 63.05 | 7.75 | 3.96 | 8.57 |
| 71 | | | 1.521 | 64.12 | 7.89 | 3.56 | 8.14 |
| | | | | 64.79 | 7.81 | 3.56 | 8.06 |
| 72 | | | 1.503 | | | | |
| 85 | | | 1.562 | | | | |
| 86 | | | 1.571 | | | | |
| 87 | | | 1.530 | | | | |
| 88 | | | 1.557 | | | | |
| 89 | | | 1.523 | | | | |
| 90 | | | 1.555 | | | | |
| 91 | | 67.2 | | | | | |
| 92 | | | 1.528 | | | | |
| 93 | | | 1.518 | | | | |
TABLE III
Compounds of the formula
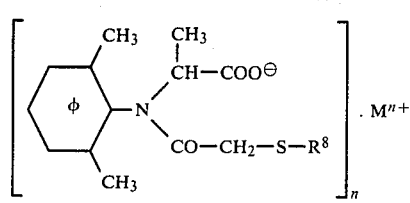
| | | | | M.p. | Values calculated, % | | | | | Values found, % | | | | |
|---|---|---|---|---|---|---|---|---|---|---|---|---|---|---|
| | $R^8$ | n | $M^{n+}$ | in °C. | C | H | N | S | cation | C | H | N | S | cation |
| 73 | H— | 1 | $H^+$ | 152 | 58.43 | 6.37 | 5.24 | 11.99 | | 58.17 | 6.49 | 5.18 | 11.80 | |
| 74 | H— | 1 | $NH_4^+$ | | 54.97 | 7.04 | 9.86 | 11.27 | | 55.03 | 7.17 | 8.42 | 11.20 | |
| 75 | H— | 1 | $Na^+$ | 124.5 | 53.98 | 5.54 | 4.84 | 11.07 | | 52.47 | 5.96 | 4.78 | 11.1 | |
| 76 | H— | 2 | $Ca^{++}$ | 245 | 54.55 | 5.59 | 4.89 | 11.19 | 6.99 | 53.34 | 5.94 | 4.72 | 10.27 | 7.1 |
| 77 | H— | 2 | $Mg^{++}$ | | 56.12 | 5.70 | 5.03 | 11.51 | 4.32 | 53.09 | 5.93 | 4.82 | 12.35 | 4.3 |
| 78 | H— | 3 | $Al^{+++}$ | 201 | 56.73 | 5.82 | 5.11 | 11.68 | 3.28 | 53.51 | 6.17 | 4.79 | 11.71 | 3.23 |
| 79 | H— | 2 | $Cu^{++}$ | 120 | 52.39 | 5.37 | 4.70 | 10.75 | 10.66 | 51.11 | 5.51 | 4.48 | 10.47 | 11.2 |
| 80 | $CH_3CO$— | 1 | $H^+$ | 140 | 58.25 | 6.15 | 4.53 | 10.36 | | 57.96 | 6.18 | 4.54 | 10.30 | |
| 81 | $CH_3CO$— | 1 | $Na^+$ | 69 | 54.38 | 5.44 | 4.23 | 9.67 | 6.95 | 52.16 | 6.23 | 4.16 | 9.92 | 6.6 |
| 82 | $CH_3CO$— | 2 | $Mg^{++}$ | 127 | 56.25 | 5.62 | 4.37 | 10 | 3.75 | 55.91 | 6.33 | 4.37 | 11.04 | 3.15 |
| 83 | $CH_3CO$— | 3 | $Al^{+++}$ | 131 | 56.78 | 5.68 | 4.42 | 10.09 | 2.84 | 54.22 | 6.04 | 4.23 | 10.09 | 2.84 |
| 84 | $CH_3CO$— | 2 | $Cu^{++}$ | 125 | 52.98 | 5.30 | 4.12 | 9.42 | 9.34 | 51.99 | 5.50 | 4.09 | 9.31 | 9.3 |

EXAMPLE 11

In vivo test using *Plasmopara viticola* on vine plants (preventive treatment)

Vine plants (GAMAY variety), cultivated in pots, are treated by spraying both sides of their leaves with an aqueous solution or aqueous emulsion containing the active ingredient to be tested (1 mg/liter); the solution or emulsion sprayed consists of the active ingredient to be tested (40 mg), water (40 cc) and Tween 80 (surface-active agent consisting of an oleate of a polyoxyethyleneated derivative of sorbitol) (0.2 cc).

This solution, made up in this way, is diluted with water to give spraying solutions having concentrations of less than 1 mg/liter of the active ingredient to be tested.

After 48 hours, contamination is carried out by spraying the underside of the leaves with an aqueous suspension of fungus spores (about 80,000 units/cc). The pots are then placed for 48 hours in an incubation cell at 100% relative humidity and at 20° C.

The plants are checked 9 days after infestation.

According to this test, the following compounds all effected a total protection when applied at a concentration of 0.11 g/liter: 1 to 22, 24, 25, 29, 30, 33 to 36, 38 to 43, 45, 47 to 53, 55 and 65 to 68; the following compounds all effected a total protection when applied at a concentration of 0.33 g/liter: 44, 46, 56, 59, 62, 76, 81, 82 and 84; the following compounds all effected a total protection when applied at a concentration of 1 g/liter: 23, 26 to 28, 32, 37, 54, 57, 60, 64, 69 to 72, 78, 79 and 83; at this same concentration of 1 g/liter, a good protection was achieved with compounds 58, 61 and 74, a fairly good protection was achieved with compound 73 and an average protection was achieved with compounds 63, 75, 77 and 80.

Of all these compounds, some (in particular compound No. 1) still exhibit a fairly good activity at very low concentrations, even at concentrations of a few mg/liter.

EXAMPLE 12

In vivo test using *Erysiphe graminis* on barley (barley oidium)

Barley, in pots, which has been sown in light agricultural earth, is treated at the 10 cm high stage by spraying it with an aqueous solution or aqueous emulsion having the same composition as that described in Example 11 and having a concentration of 1 g/liter. The experiment is repeated twice. After 48 hours, the barley plants are sprinkled with spores of *Erysiphe graminis*, the sprinkling being carried out with the aid of diseased plants.

The results are observed 8 days after contamination.

Under these conditions, a total protection of the barley plants is observed in the case of compound No. 47, a good protection is observed in the case of compound No. 6 and a fairly good protection is observed in the case of compound No. 61.

EXAMPLE 13

In vivo test using "*Puccinia striiformis*", which is responsible for wheat rust Wheat, in pots, which has been sown in light agricultural earth, is treated at the 10 cm high stage by spraying it with an aqueous solution or aqueous emulsion having the same composition as that described in Example 11 and having a concentration of 1 g/liter. The experiment is repeated twice.

After 48 hours, an aqueous suspension of spores (50,000 spores/cc) is sprayed onto the wheat; this suspension has been obtained from contaminated plants. The wheat is then placed for 48 hours in a climatic cell regulated in the following manner: illumination: 16 hours/day; temperature: 20° C. by day and 15° C. by night; relative humidity: 100%.

After these 2 days, the relative humidity is lowered to 60%. The condition of the plants is checked, 15 days after contamination, by comparison with the untreated control plant.

Under these conditions, a total protection of the wheat is observed in the case of compounds Nos. 26 and 48 and a good protection is observed with compounds Nos. 15, 17, 25, 28, 30, 43, 52, 57, 60, 61, 71 and 77.

EXAMPLE 14

In vivo test using "*Phytophtora infestans*", which is responsible for tomato mildew Tomato plants (Marmande variety), which have been cultivated in a greenhouse and are 60 to 75 days old, are treated by spraying them with aqueous solutions or aqueous emulsions prepared as indicated in Example 11 and containing various concentrations of the active ingredient to be tested.

After 48 hours, the treated plants are contaminated with an aqueous suspension of spores (zoo sporangia), obtained from a "*Phytophtora infestans*" culture cultivated for 20 days on a medium based on flour of chickpeas.

The tomato plants are placed for 48 hours in an enclosure which is at a temperature of 16° to 18° C. and is provided with an atmosphere having a relative humidity of 100%, and the relative humidity is then lowered to 80%.

The results are observed 8 days after contamination in a cell provided with an atmosphere having a relative humidity of 80%. The results are assessed by evaluating the surface area of the leaves which has been infested by the fungus, and are expressed as the "percentage protection", i.e.

$$100\left(1 - \frac{S}{Sc}\right),$$

S being the surface area infested by the fungus on the plant in question and Sc being the surface area infested by the fungus on the untreated control plant. As in the preceding examples, the results are indicated below in the form of total, good, fairly good or average protection.

Under these conditions and using an aqueous solution having a concentration of 1 g/liter of the active ingredient to be tested, a total protection was observed in the case of compounds Nos. 2, 3, 12, 14, 15, 19, 22, 23, 31, 50 and 52 and a good protection was observed in the case of compounds Nos. 17 and 45.

At a concentration of 0.11 g/liter, a total protection was observed in the case of compounds Nos. 16 and 66 and a good protection was observed in the case of compounds Nos. 24 and 38.

These experiments clearly illustrate the remarkable fungicidal properties of the compounds according to the invention, especially against fungi of the Phycomycetes type (mildew), and also their lack of phytotoxicity; their high activity, even at low doses, is totally remarkable. These compounds can therefore be used for combating fungal diseases (in particular mildews), in both a preventive and a curative capacity, in plants in general and, in particular, in vine, tobacco, hop, tomato, potato and sunflower plants and market-garden crops in general.

Furthermore, the compounds of the invention can also be used to combat fungal diseases in other plants, especially cereals and more especially wheat and barley.

For their use in practice, the compounds according to the invention are rarely employed by themselves. Most frequently, they form part of compositions. These compositions, which can be used for protecting plants against fungal diseases, contain, as the active ingredient, a compound according to the invention, as described above, in association with solid or liquid carriers which are acceptable in agriculture and surface-active agents which are also acceptable in agriculture. In particular, the customary inert carriers and the customary surface-active agents can be used.

These compositions can also contain any kind of other ingredients such as, e.g. protective colloids, adhesives, thickeners, thixotropic agents, penetrating agents, stabilizers, sequestering agents and the like, and also other known active ingredients having pesticidal (in particular insecticidal or fungicidal) properties, properties which favour the growth of the plants (in particular fertilisers) or properties which regulate the growth of the plants. More generally, the compounds according to the invention can be associated with all the solid or liquid additives corresponding to the usual formulation techniques.

The use doses of the compounds according to the invention can vary within wide limits, depending in particular on the virulence of the fungi and on the climatic conditions.

In general terms, compositions containing 0.5 to 5,000 ppm of active ingredient are very suitable; these values are indicated for ready-to-use compositions. Ppm means "parts per million". The 0.5 to 5,000 ppm range corresponds to a range of $5 \times 10^{-5}$ to 0.5% (percentages by weight).

As regards the compositions suitable for storage and transportation, they more advantageously contain from 10 to 95% (by weight) of active ingredient.

Thus, the compositions for agricultural use, according to the invention, can contain the active ingredients according to the invention in amounts which vary within very wide limits ranging from $5.10^{-5}$% to 95% (by weight).

As already stated, the compounds according to the invention are generally associated with carriers and, if appropriate, surface-active agents.

In the present account, the term "carrier" denotes an organic or inorganic, natural or synthetic material with which the active ingredient is associated in order to facilitate its application to the plant, to seeds or to the soil. This carrier is therefore generally inert and it must be acceptable in agriculture, in particular to the plant treated. The carrier can be solid (clays, natural or synthetic silicates, silica, resins, waxes, solid fertilizers or the like) or liquid (water, alcohols, ketones, petroleum fractions, aromatic or paraffinic hydrocarbons, chlorohydrocarbons, liquefied gases or the like).

The surface-active agent can be an emulsifying agent, dispersing agent or wetting agent of the ionic or non-ionic type. Examples which may be mentioned are salts of polyacrylic acids, salts of lignosulphonic acids salts of phenolsulphonic or naphthalenesulphonic acids, products resulting from the polycondensation of ethylene oxide with fatty alcohols, fatty acids or fatty amines, substituted phenols (in particular alkylphenols or arylphenols), salts of sulphosuccinic acid esters, taurine derivatives (in particular alkyltaurates) and phosphoric acid esters of polyoxyethyleneated alcohols or phenols. The presence of at least one surface-active agent is generally essential if the active ingredient and/or the inert carrier are not soluble in water and if the vehicle of application is water.

For their application, the compounds of the formula (I) are therefore generally in the form of compositions; these compositions according to the invention are themselves in fairly varied solid or liquid forms.

Forms of solid compositions which may be mentioned are dusting powders or dispersing powders (in which the proportion of the compound of the formula (I) can range up to 100%) and granules, in particular those obtained by extrusion, by compaction, by impregnation of a granular carrier or by the formation of granules from a powder (the proportion of the compound of the formula (I) in these granules being between 1 and 80% in these last cases).

As forms of compositions which are liquid or are to be made into liquid compositions for application, there may be mentioned solutions, in particular water-soluble concentrates, emulsifiable concentrates, emulsions, suspension concentrates, aerosols, wettable powders (or spraying powders) and pastes.

The emulsifiable or soluble concentrates most frequently comprise 10 to 80% of active ingredient, whilst the ready-to-use emulsions or solutions contain 0.01 to 20% of active ingredient. In addition to the solvent, the emulsifiable concentrates can contain, if necessary, 2 to 20% of suitable additives such as stabilizers, surface-active agents, penetrating agents, corrosion inhibitors, dyestuffs and adhesives. The compositions of a few concentrates are now given by way of example:

| | |
|---|---|
| active ingredient | 400 g/liter |
| alkali metal dodecylbenzenesulphonate | 24 g/liter |
| oxyethyleneated nonylphenol containing 10 molecules of ethylene oxide | 16 g/liter |
| cyclohexanone | 200 g/liter |
| aromatic solvent | q.s.p 1 liter |

According to another formulation of an emulsifiable concentrate, the following composition is used:

| | |
|---|---|
| active ingredient | 250 g |
| epoxidized vegetable oil | 25 g |
| mixture of an alkylarylsulphonate and a polyglycol ether of fatty alcohols | 100 g |
| dimethylformamide | 50 g |
| xylene | 575 g |

Using these concentrates, emulsions of any desired concentration, which are particularly suitable for application to leaves, can be obtained by dilution with water.

The suspension concentrates, which can also be applied by spraying, are prepared so as to give a stable fluid product which does not form a deposit, and they usually contain from 10 to 75% of active ingredient, from 0.5 to 15% of surface-active agents, from 0.1 to 10% of thixotropic agents, from 0 to 10% of suitable additives, such as anti-foam agents, corrosion inhibitors, stabilizers, penetrating agents and adhesives, and, as the carrier, water or an organic liquid in which the active ingredient is sparingly soluble or insoluble; certain organic solids or inorganic salts can be dissolved in the carrier in order to prevent sedimentation or to act as anti-freeze agents for the water.

The wettable powders (or spraying powders) are usually prepared so that they contain 20 to 95% of active ingredient, and they usually contain, in addition to the solid carrier, from 0 to 5% of a wetting agent, from 3 to 10% of a dispersing agent and, if necessary, from 0 to 10% of one or more stabilizers and/or other additives such as penetrating agents, adhesives or anti-caking agents, dyestuffs and the like.

Various compositions of wettable powders are now given by way of example:

| active ingredient | 50% |
|---|---|
| calcium lignosulphonate (deflocculant) | 5% |
| isopropylnaphthalenesulphonate (anionic wetting agent) | 1% |
| anti-caking silica | 5% |
| kaolin (filler) | 39% |

Another composition of a 70% strength spraying powder uses the following constituents:

| active ingredient | 700 g |
|---|---|
| sodium dibutylnaphthylsulphonate | 50 g |
| product resulting from the condensation of naphthalenesulphonic acid, phenol-sulphonic acid and formaldehyde in proportions of 3:2:1 | 30 g |
| kaolin | 100 g |
| Champagne chalk | 120 g |

Another composition of a 40% strength spraying powder uses the following constituents:

| active ingredient | 400 g |
|---|---|
| sodium lignosulphonate | 50 g |
| sodium dibutylnaphthalenesulphonate | 10 g |
| silica | 540 g |

Another composition of a 25% strength spraying powder uses the following constituents:

| active ingredient | 250 g |
|---|---|
| calcium lignosulphonate | 45 g |
| mixture of equal amounts by weight of Champagne chalk and hydroxyethylcellulose | 19 g |
| sodium dibutylnaphthalenesulphonate | 15 g |
| silica | 195 g |
| Champagne chalk | 195 g |
| kaolin | 281 g |

Another composition of a 25% strength spraying powder uses the following constituents:

| active ingredient | 250 g |
|---|---|
| isooctylphenoxy-polyoxyethylene-ethanol | 25 g |
| mixture of equal amounts by weight of Champagne chalk and hydroxyethylcellulose | 17 g |
| sodium aluminosilicate | 543 g |
| kieselguhr | 165 g |

Another composition of a 10% strength spraying powder uses the following constituents:

| active ingredient | 100 g |
|---|---|
| mixture of sodium salts of saturated fatty acid sulphates | 30 g |
| product resulting from the condensation of naphthalenesulphonic acid and formaldehyde | 50 g |
| kaolin | 820 g |

To obtain these spraying powders or wettable powders, the active ingredients are intimately mixed with the additional substances in suitable mixers and the resulting mixture is ground with mills or other suitable grinders. This gives spraying powders having advantageous wettability and suspendibility properties; they can be suspended in water at any desired concentration and this suspension can be used very advantageously, in particular for application to the leaves of plants.

Pastes can be produced instead of wettable powders. The conditions and procedures for the production and use of these pastes are similar to those for the wettable powders or spraying powders.

As already stated, aqueous dispersions and aqueous emulsions, e.g. compositions obtained by diluting, with water, a wettable powder or an emulsifiable concentrate according to the invention, fall within the general scope of the present invention. The emulsions can be of the water-in-oil or oil-in-water type and they can have a thick consistency such as that of a "mayonnaise".

The granules, which are intended to be placed on the soil, are usually prepared so that they have sizes of between 0.1 and 2 mm, and they can be manufactured by agglomeration or impregnation. In general, the granules contain 0.5 to 25% of active ingredient and 0 to 10% of additives such as stabilizers, slow-release modifiers, binders and solvents.

According to an example of the composition of granules, the following constituents are used:

| active ingredient | 50 g |
|---|---|
| epichlorohydrin | 2.5 g |
| cetyl polyglycol ether | 2.5 g |
| polyethylene glycol | 35 g |
| kaolin (particle size: 0.3 to 0.8 mm) | 910 g |

In this particular case, the active ingredient is mixed with the epichlorohydrin and the mixture is dissolved in acetone (60 g); the polyethylene glycol and the cetyl polyglycol ether are then added. The kaolin is sprayed with the resulting solution and the acetone is then evaporated off in vacuo. Microgranules of this kind are advantageously used to combat soil fungi.

The compounds of the formula (I) can also be used in the form of dusting powders; it is also possible to use a composition comprising active ingredient (50 g) and talc (950 g); it is also possible to use a composition comprising active ingredient (20 g), finely divided silica (10 g) and talc (970 g); these constituents are mixed and ground and the mixture is applied by dusting.

We claim:

1. A compound, useful as a pesticide, of the formula:

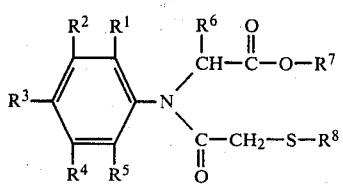

in which
- $R^1$ and $R^5$, which are identical or different, represent an alkyl or alkoxy radical having from 1 to 4 carbon atoms or a halogen atom or the hydrogen atom, it being possible for only one of the two radicals $R^1$ or $R^5$ to have this last meaning,
- $R^2$, $R^3$ and $R^4$, which are identical or different, represent the hydrogen atom or a halogen atom or an alkyl or alkoxy radical having from 1 to 4 carbon atoms,
- $R^6$ represents the hydrogen atom or a methyl radical,
- $R^7$ represents the hydrogen atom or an alkyl radical having from 1 to 12 carbon atoms and
- $R^8$ represents a radical of the formula $R^9$—CO—, in which $R^9$ is an organic radical which represents a linear or branched alkyl or alkenyl radical which has at most 18 carbon atoms and can be substituted by halogen atoms or hydroxyl, mercaptan, cyano or oxo groups or alkoxy, alkylthio, aryl, alkoxycarbonyl or alkanoylamino radicals, these various radicals having at most 6 carbon atoms, a cycloalkyl radical which contains 3 to 7 carbon atoms in the ring and can be substituted by halogen atoms or alkyl groups having at most 4 carbon atoms, a phenyl or naphthyl radical which is optionally substituted by halogen atoms or alkyl, alkanoyloxy, alkanoyl or alkoxy groups, these various groups having at most 6 carbon atoms.

2. A compound according to claim 1, in which $R^7$ represents an alkyl group having 1 to 12 carbon atoms and the halogen atoms are chlorine or bromine.

3. A compound according to claim 1 in which $R^2$ represents a hydrogen, chlorine or bromine atom, $R^3$ and $R^4$ represent the hydrogen atom and $R^1$ and $R^5$ represent an alkyl group having from 1 to 4 carbon atoms.

4. A compound according to one of claims 1 or 3 in which $R^1$, $R^5$ and $R^7$ are the methyl radical and $R^9$ is an alkyl radical having from 1 to 9 carbon atoms.

5. A product according to claim 1 or 3 in which $R^1$, $R^5$ and $R^7$ are each the methyl radical.

6. A compound according to claim 1 or 3 wherein $R^9$ is an alkyl radical having 1 to 9 carbon atoms.

7. A composition useful for protecting plants against fungal diseases comprising as the active ingredient, a fungicidally effective amount of a compound according to one of claims 1, 2, 3, 5 or 6, in association with an inert carrier and optionally, an agriculturally acceptable surface-active agent.

8. A composition according to claim 7, which contains $5.10^{-5}$ to 95% of active ingredient.

9. A process for combatting fungal diseases in plants, comprising applying to said plants a fungicidally effective amount of a composition defined in claim 7.

* * * * *